(12) United States Patent
Sasson et al.

(10) Patent No.: US 10,207,921 B2
(45) Date of Patent: Feb. 19, 2019

(54) METHOD FOR STORAGE AND RELEASE OF HYDROGEN

(71) Applicant: YISSUM RESEARCH DEVELOPMENT COMPANY OF THE HEBREW UNIVERSITY OF JERUSALEM LTD., Jerusalem (IL)

(72) Inventors: Yoel Sasson, Jerusalem (IL); Harold Wiener, Jerusalem (IL); Ariel Givant, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 348 days.

(21) Appl. No.: 15/034,578

(22) PCT Filed: Nov. 5, 2014

(86) PCT No.: PCT/IL2014/050965
§ 371 (c)(1),
(2) Date: May 5, 2016

(87) PCT Pub. No.: WO2015/068161
PCT Pub. Date: May 14, 2015

(65) Prior Publication Data
US 2016/0272490 A1 Sep. 22, 2016

Related U.S. Application Data

(60) Provisional application No. 61/900,432, filed on Nov. 6, 2013.

(51) Int. Cl.
*C07C 53/06* (2006.01)
*C01B 3/22* (2006.01)
(Continued)

(52) U.S. Cl.
CPC .............. *C01B 3/22* (2013.01); *B01J 21/18* (2013.01); *B01J 23/44* (2013.01); *B01J 23/96* (2013.01);
(Continued)

(58) Field of Classification Search
None
See application file for complete search history.

(56) References Cited

U.S. PATENT DOCUMENTS 4,067,958 A * 1/1978 Gorin ................. B01J 27/047
423/246
4,137,298 A * 1/1979 Zielke ................. C01B 3/22
423/655

(Continued)

FOREIGN PATENT DOCUMENTS

CN 101347730 A 1/2009
CN 102294240 A 12/2011
(Continued)

OTHER PUBLICATIONS

H. Wiener et al., "The Heterogeneous Catalytic Hydrogenation of Bicarbonate to Formate in Aqueous Solutions", Journal of Catalysis, vol. 110 (1988) pp. 184-190.
(Continued)

*Primary Examiner* — Wayne A Langel
(74) *Attorney, Agent, or Firm* — Millen White Zelano & Branigan, PC (57) ABSTRACT

The invention provides a process for the production of hydrogen, comprising catalytically decomposing a concentrated aqueous solution of potassium formate in a reaction vessel to form bicarbonate slurry and hydrogen, discharging the hydrogen from said reaction vessel, and treating a mixture comprising the bicarbonate slurry and the catalyst
(Continued)

with an oxidizer, thereby regenerating the catalyst. Pd/C catalysts useful in the process are also described.

17 Claims, 8 Drawing Sheets

(51) Int. Cl.
| | |
|---|---|
| *C01B 3/00* | (2006.01) |
| *H01M 8/0606* | (2016.01) |
| *B01J 23/44* | (2006.01) |
| *B01J 38/12* | (2006.01) |
| *B01J 38/48* | (2006.01) |
| *B01J 38/64* | (2006.01) |
| *B01J 23/96* | (2006.01) |
| *B01J 35/00* | (2006.01) |
| *B01J 21/18* | (2006.01) |
| *B01J 37/03* | (2006.01) |
| *B01J 37/16* | (2006.01) |
| *B01J 38/70* | (2006.01) |

(52) U.S. Cl.
CPC .......... *B01J 35/002* (2013.01); *B01J 35/006* (2013.01); *B01J 37/035* (2013.01); *B01J 37/16* (2013.01); *B01J 38/12* (2013.01); *B01J 38/48* (2013.01); *B01J 38/64* (2013.01); *B01J 38/70* (2013.01); *C01B 3/0015* (2013.01); *C01B 3/0073* (2013.01); *C07C 53/06* (2013.01); *H01M 8/0606* (2013.01); *C01B 2203/0277* (2013.01); *C01B 2203/066* (2013.01); *C01B 2203/1064* (2013.01); *C01B 2203/1082* (2013.01); *Y02E 60/328* (2013.01); *Y02P 20/584* (2015.11)

(56) References Cited

U.S. PATENT DOCUMENTS 9,169,281 B2   10/2015   Fukuzumi

2004/0022716 A1*   2/2004   Mahajan .............. B01J 31/1805
423/418.2
2011/0158899 A1*   6/2011   Nakahara .................. C01B 3/22
423/648.1
2011/0172082 A1   7/2011   Quinn et al.

FOREIGN PATENT DOCUMENTS

| DE | 102006030449 A1 | | 1/2007 |
| DE | 102008033324 A1 | | 2/2009 |
| WO | WO 88/05422 | * | 7/1988 |
| WO | 2011108730 A1 | | 9/2011 |

OTHER PUBLICATIONS

English translation of Notification of Reason(s) for Refusal in corresponding Japan Patent Application No. 2016-551111 dispatched May 8, 2018. (pp. 1-6).
International Search Report dated Mar. 2, 2015 issued in corresponding PCT/IL2014/050965 application (pp. 1-6).
Written Opinion of the International Searching Authority dated Mar. 2, 2015 issued in corresponding PCT/IL2014/050965 application (pp. 1-12).
H. Kramer et al., "Hydrogen Storage by the Bicarbonate/Formate Reaction. Studies on the Activity of Pd Catalysts", International Journal of Hydrogen Energy, vol. 20, No. 3 (1995) pp. 229-233.
H. Wiener et al., "Storage of Energy by Solutions of Alkali Formate Salts", Solar Energy, vol. 43, No. 5 (1989) pp. 291-296.
B. Zaidman et al., "Formate Salts as Chemical Carriers in Hydrogen Storage and Transportation", International Journal of Hydrogen Energy, vol. 11, No. 5 (1986) pp. 341-347.
English Abstract of DE 102006030449 A1 published Jan. 4, 2007.
English Abstract of DE 102008033324 A1 published Feb. 19, 2009.
English Translation of Chinese Search Report dated Jun. 6, 2017 issued in corresponding CN 201480071642.9 application.
English Machine Translation of CN 101347730 A published Jan. 21, 2009.
English Machine Translation of CN 102294240 A published Dec. 28, 2011.

* cited by examiner

METHOD FOR STORAGE AND RELEASE OF HYDROGEN

FIELD OF THE INVENTION

The invention relates to a method for providing hydrogen in a storable and transportable form, based on the bicarbonate-formate cyclic system.

BACKGROUND OF THE INVENTION

The bicarbonate-formate cycle has been described by Zaidman, Weiner and Sasson [Int. J. Hydrogen Energy, 11(5), pp. 341-347 (1986) and Weiner, Blum, Feilchenfeld, Sasson and Zalmanov [Journal of Catalysis, 110, pp. 184-190 (1988)], suggesting the use of aqueous formate solutions as hydrogen carriers. The bicarbonate-formate cycle consists of two stages, as shown by the following chemical equation:

$$HCO_3^- + H_2 \leftrightarrow HCO_2^- + H_2O$$

The first stage involves the reduction of bicarbonate to formate. To this end, a bicarbonate salt in aqueous solution is reacted with hydrogen at about 35° C. under hydrogen pressure, to give an aqueous solution of the corresponding formate salt. On demand, the reverse reaction is carried out, normally at about 70° and atmospheric pressure, whereby the formate is decomposed to produce the bicarbonate and hydrogen. The hydrogen can then be used for any desired purpose, e.g., as a fuel material. It follows that in the first stage (formate synthesis), the system is loaded with hydrogen, which is released and delivered in the second stage (formate decomposition). Both stages are carried out in the presence of a catalyst, e.g. heterogeneous catalyst such as palladium.

Kramer, Levy and Warshawsky [Int. J. Hydrogen Energy, 20(3), pp. 229-233 (1995)] investigated the activity of the catalysts used in bicarbonate-formate cycle, starting by reacting 3.5 M $KHCO_3$ solution with hydrogen to give the formate. The authors reported that the activity of the palladium catalyst used decreases with time, demonstrating that the catalyst can be regenerated through the following sequence of steps: (i) separating the catalyst from the solution; (ii) washing with distilled water at ambient temperature; (iii) drying at 120° C. under argon atmosphere; (iv) oxidizing the catalyst with oxygen or air.

It would be beneficial to provide a process allowing enhanced hydrogen storage and production capacity, and on the same time, offering a convenient way for treating and regenerating the catalyst used.

THE INVENTION

Figure 1:
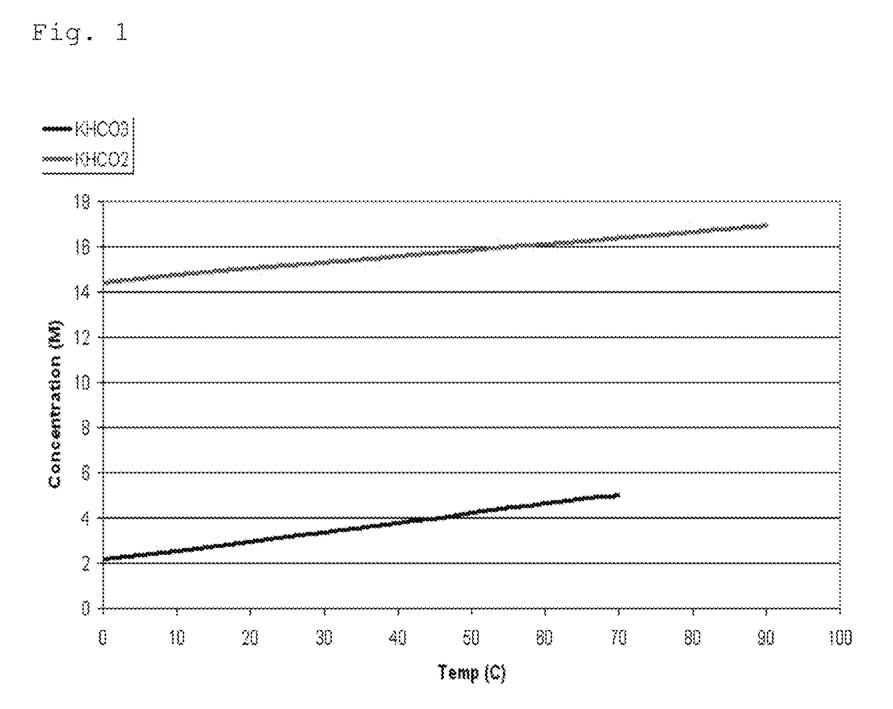
FIG. 1 shows the solubility curves of potassium bicarbonate and potassium formate.

The dependence of solubility on temperature was investigated for potassium bicarbonate and potassium formate in the temperature ranges from 0 to 70° C. and 0 to 90° C., respectively. The solubility curves are graphically presented in FIG. 1, indicating that potassium bicarbonate is significantly less soluble in water in comparison to potassium formate. The results suggest that the reduced solubility of potassium bicarbonate in comparison to potassium formate may introduce a serious limitation into the bicarbonate-formate system from the perspective of hydrogen storage capacity.

The inventors found that the catalytically-driven bicarbonate-formate storage cycle can be generated starting with a bicarbonate slurry (in lieu of a bicarbonate solution), which upon reaction with hydrogen gives highly concentrated aqueous formate solution. The catalytic decomposition of this formate solution yields back the bicarbonate slurry and hydrogen. Surprisingly, the bicarbonate slurry, which consists of a solid mixture of the bicarbonate salt, the catalyst and a small amount of water, permits an easy regeneration of the catalyst. The regeneration is accomplished by exposing the slurry to air or oxygen, e.g., at elevated temperature under vigorous mixing, whereby the catalyst regains its activity.

By the term "bicarbonate slurry", as used herein, is meant one or more bicarbonate salts in a solid form (e.g., solid $KHCO_3$), preferably in a mixture with water. The weight ratio between the solid bicarbonate component and the aqueous phase of the bicarbonate slurry is preferably not less than 1:1 and more preferably not less than 2:1.

The present invention is therefore directed to a process for the production of hydrogen, comprising catalytically decomposing a concentrated aqueous solution of potassium formate in a reaction vessel to form bicarbonate slurry and hydrogen, discharging the hydrogen from said reaction vessel, and treating a mixture comprising the bicarbonate slurry and the catalyst with an oxidizer, thereby regenerating said catalyst. Formate decomposition to generate hydrogen can be advanced under heating, but also at ambient temperature, in an acidic environment. More specifically, the decomposition of formate takes place at a temperature above 50° C., e.g., in the range 50 to 70° C., or at a temperature below 50° C., e.g., in the range 0 to 45° C., with the aid of an acid.

The present invention is also directed to a process for the storage of hydrogen, comprising treating a mixture of potassium bicarbonate slurry and a catalyst with an oxidizer, and catalytically reducing said bicarbonate slurry in a reaction vessel to form a concentrated aqueous solution of potassium formate.

Another aspect of the present invention relates to the use of bicarbonate slurry in admixture with catalyst particles in the heterogeneous catalytic hydrogenation of bicarbonate to formate. The slurry is periodically treated with an oxidizer, whereby the catalyst is regenerated.

More specifically, the present invention is directed to a process for storage and subsequent release of hydrogen, comprising:
(i) catalytically hydrogenating in a reaction vessel a potassium bicarbonate slurry to form a concentrated aqueous solution of potassium formate;
(ii) catalytically decomposing said formate solution in a reaction vessel to form a bicarbonate slurry and hydrogen;
(iii) discharging the hydrogen from said second reaction vessel, and
(iv) treating a mixture comprising said bicarbonate slurry and the catalyst with an oxidizer, thereby regenerating said catalyst.

The process of the invention involves the synthesis of an aqueous solution of potassium formate through the heterogeneous catalytic reduction of a potassium bicarbonate slurry. To this end, the bicarbonate salt and water are charged into a suitable reaction vessel, followed by the addition of a catalyst. It should be noted, however, that the catalyst normally contains some water. The water content of the catalyst may suffice for the purpose of slurry formation, such that the addition of water to the reaction vessel is unnecessary. The reaction vessel is capable of withstanding high pressures (e.g., high pressure autoclave). An especially preferred bicarbonate salt is potassium bicarbonate. The amounts of the bicarbonate salt and water are adjusted as set forth above, forming a slurry in the reaction vessel.

Catalysts operable in the process include palladium or supported palladium, e.g., palladium supported on carbon. Palladium on PANI (polyaniline), palladium on CNT (carbon nano tubes) and palladium on montmorillonite treated in ionic liquid (montmorillonite suspended in ionic liquid and then filtered before being used as palladium support) are also useful in the process of the invention. The preparation of different forms of supported palladium catalysts is illustrated in the working examples below. Suitable catalysts are also commercially available from Engelhard, Johnson Matthey, and Sigma-Aldrich. The molar ratio between the bicarbonate salt and the catalyst is in the range from 50:1 to 1000:1, preferably about 200:1 to 700:1.

The conversion of the bicarbonate to formate is accomplished in the presence of hydrogen. Thus, hydrogen is fed to the reaction vessel at a temperature in the range from 25° C. to 70° C., preferably at about 35° C., to pressure of about 4-25 atmospheres. The reaction mixture is maintained under stirring for not less than 1 hour, e.g., about 2 hours, thereby completing the formate synthesis. The concentration of the formate salt in the resulting solution is not less than 4M, preferably not less than 5M and more preferably not less than 8M, and may be up to saturation. For example, from 8.0 to 15.7 M (measured at room temperature; the solubility limit of formate at 70° C. is 16 M). When terms such as "a concentrated aqueous solution of potassium formate" are used herein, then a solution with the concentration characteristics set forth above is intended (e.g., with concentration of not less than 4M, preferably not less than 5M, and more preferably not less than 8M, etc.).

It should be noted that the hydrogen employed in the first stage of the process may be either from a commercially available cylinder, in which case the process of the invention is chiefly utilized for converting the gaseous hydrogen into a "latent" form, i.e., the formate aqueous carrier, which is more easy and safe to handle for storage and transportation. However, the hydrogen may be produced in situ, e.g., by means of electrochemical methods, following which the hydrogen which evolves on the electrode is directly absorbed by the bicarbonate slurry.

The process of the invention involves the decomposition of the aqueous formate solution, for generating hydrogen. It should be understood that in many cases, the synthesis and decomposition of the formate are both carried out in the same reaction vessel (namely, in a single reaction vessel). However, in those cases where the formate solution is produced in one place and subsequently transferred to another place, i.e., to a site of its intended use, then the reaction vessels used for storage and release of hydrogen may be different.

The decomposition of the formate is carried out under atmospheric pressure at a temperature which is preferably not less than 0° C., e.g., in the range 0 to 45° C., with the aid of an acid (for example, at a temperature from 15° C. to 30° C.), or in the range from 50° C. and 70° C. when the process is devoid of acidification. The decomposition reaction lasts not less than 30 minutes, e.g., about 45 minutes. The molar ratio between the formate salt and the catalyst is in the range from 50:1 to 1000:1, preferably about 200:1 to 700:1.

Upon completion of the decomposition step, the hydrogen gas produced is discharged from the reaction vessel and is delivered to, and utilized in, for example, an electricity-generating system, e.g., a fuel cell involving the use of hydrogen. An example is illustrated in FIG. 3, which is described below.

Following hydrogen discharge, the reaction mass left in the reactor consists of a bicarbonate slurry in admixture with the catalyst particles. The slurry is treated with an oxidizer, which is most preferably air or oxygen. The oxidizer gas is fed to the reactor to pressures of not less than 1 atm., e.g., from 1 atm. to 10 atm., and the content of the reactor is thoroughly mixed, such that the catalyst particles are exposed to the oxidizer. For example, the mixing can be carried out using a screw impeller. The regeneration step is preferably carried out at a temperature of not less than 50° C., for at least 60 minutes. Following the regeneration step, the slurry may be used in the synthesis of formate aqueous solution, as set forth above. It should be noted that the foregoing catalyst treatment is carried out periodically, i.e., the reversible catalytic hydrogenation and dehydrogenation are allowed to run in a cyclic manner for several times until the need for catalyst regeneration arises.

Figure 3:
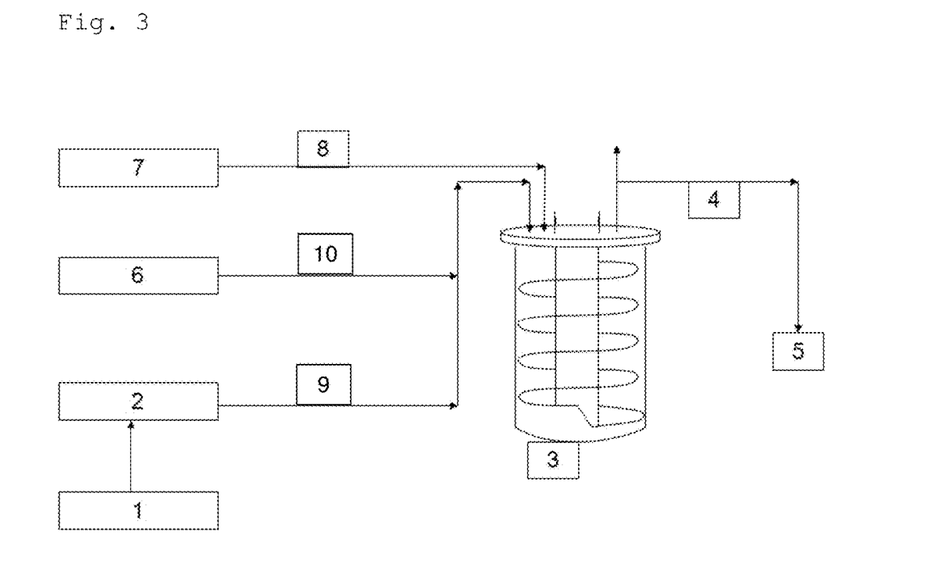
FIG. 3 schematically illustrates an apparatus for carrying out the process of the invention.

FIG. 3 schematically illustrates one embodiment of the process of the invention. In the first stage (formate synthesis), hydrogen generated in an electrolytic cell (1) is compressed in a compressor (2) to the desired working pressure and then fed via feed line (9) into a reaction vessel (3) charged with a bicarbonate slurry and a catalyst. The hydrogen is fed to pressure of up to 25 atmospheres. The reaction vessel is equipped with suitable agitation means and heating means. The formate synthesis is carried out under the conditions set forth above. On demand, the formate is decomposed under atmospheric pressure to form hydrogen and bicarbonate slurry in admixture with the catalyst particles. The hydrogen is released from the reactor through pipe (4) and delivered to a fuel cell (5), where it is oxidized (e.g., through the use of oxygen) to generate an electric current. Following hydrogen removal from the reactor and prior to the next step of formate synthesis, air is introduced into the reactor to pressure of up to 10 atmospheres, from air compressor (6), via feed line (10). Under through mixing, the catalyst is oxidized and regenerated such that it can effectively catalyze a subsequent formate formation reaction.

The process described above involves the conversion of a bicarbonate slurry into highly concentrated aqueous solution of the corresponding formate salt, from which hydrogen can be subsequently liberated (e.g., potassium bicarbonate→potassium formate). However, it has been also found that hydrogen can be effectively stored and released from a formate slurry, e.g., from a sodium formate slurry (sodium formate is much less soluble in water than potassium formate). Thus, the invention also relates to a process comprising catalytically decomposing a formate slurry, to form the corresponding bicarbonate and hydrogen. Following the release of hydrogen, the resultant mixture of bicarbonate and catalyst particles can be treated with air as described above, in order to refresh the catalyst.

We have also investigated the effect of acid addition on the dehydrogenation of potassium formate over Pd/C. It should be noted that acidification of the reaction medium causes the following undesired reaction of bicarbonate decarboxylation (equation no.2):

$$HCO_2^- + H_2O \rightarrow HCO_3^- + H_2 \qquad 1.$$

$$HCO_3^- + H_3O^+ \rightarrow 2H_2O + CO_2 \qquad 2.$$

The result of bicarbonate decarboxylation is a loss of $CO_2$ and irreversibility for hydrogen storage. In order to store hydrogen again we have to supply $CO_2$ and invest energy to recover bicarbonate from carbonate.

We have found that the process is still manageable in an acidic environment to achieve useful results which compensate for some decrease in the storage capacity of the system caused by the evolvement and loss of carbon dioxide. On selection of suitable acidic conditions, the dehydrogenation of potassium formate over Pd/C occurs at surprisingly increased rates at reduced temperature (T<70° C., e.g., from 0 to 50° C.). The enhanced reaction rates attainable in an acidic environment even at ambient temperature lead to a rapid generation of hydrogen on demand. Thus, instantaneous hydrogen release is possible on account of the fact that there is no need to apply heating to accelerate the reaction. The hydrogen gas which rapidly evolves on acidification of the formate solution can be utilized at once as a fuel material in a fuel cell coupled to systems in need for an immediate power supply, e.g., emergency backup electrical generators powered by fuel cells.

The properties considered important for screening potentially useful acids for acidifying the formate solution are the turnover numbers at deactivation (TONs) and turnover frequencies (TOFs) measured for the catalytically-driven formate decomposition reaction, indicative of the catalyst activity. In the experimental work reported below, a variety of acids were tested for their ability to advance the reaction, namely, mineral acids such hydrogen chloride, nitric acid and sulfuric acid, and organic acids such as acetic acid and formic acid, with the latter emerging as the best choice.

The acidification of the reaction medium can be achieved by addition of an acid to the aqueous formate solution, by incorporation of a solid acid into the heterogeneous catalyst (can be used in a continuous reactor) or by acid treatment to the carbon support of the palladium catalyst. In general, the pH of the aqueous formate solution is adjusted within the range from 3 to 6.

In the presence of an acid, especially formic acid, the decomposition of potassium formate proceeds efficiently to generate hydrogen at a temperature below 50° C., e.g., in the range from 0 to 45° C. For example, within the temperature range below room temperature, i.e., less than 15° C., TON and TOF exceeding 500 and 20, respectively, were measured, as illustrated by the experimental work reported below. It should be noted that even highly concentrated potassium formate solutions can benefit from the presence of an acid, i.e., the acidification allows a swift production of hydrogen within the temperature range of 15 to 45° C. starting with solutions having potassium formate concentration as high as 8M-15M, e.g., 10M-13M.

The molar ratio between potassium formate and formic acid appears to be an important process variable. On plotting the TON measured (at deactivation) against the molar ratio potassium formate:formic acid (abbreviated $MR_{PF:FA}$), a curve resembling the graphic description of an inverted parabola is obtained, with an axis of symmetry lying in the range from $10:1 \leq MR_{PF:FA} \leq 10:10$. The exact $MR_{PF:FA}$ value for which a maximal TON is measured may depend on factors such the temperature of the reaction and concentration of the potassium formate solution. For example, for potassium formate decomposition taking place at about room temperature, high TON (e.g., exceeding 500) are achieved when the $MR_{PF:FA}$ is adjusted within the range from 10:2 to 10:6 for 5M to 15M potassium formate solution.

Accordingly, another aspect of the invention is a process for the production of hydrogen, comprising catalytically decomposing potassium formate in a concentrated aqueous solution in the presence of an acid, which is preferably formic acid, at a temperature below 50° C., e.g., from 0 to 45° C. (for example, from 15 to 30° C., i.e., at ambient temperature), to form bicarbonate slurry and hydrogen, discharging the hydrogen from said reaction vessel, and treating a mixture comprising the bicarbonate slurry and the catalyst with an oxidizer, thereby regenerating said catalyst. The concentration of the aqueous potassium formate solution is not less than 4 M, and the molar ratio potassium formate to the acid is from 10:1 to 10:10, preferably from 10:2 to 10:6.

In one embodiment of the invention, the process comprises the step of adding an acid (e.g., HCOOH) to the concentrated potassium formate solution and carrying out the decomposition reaction at ambient temperature, i.e., without heating the potassium formate solution. Returning to the apparatus illustrated in FIG. 3, the addition of the acid may be actuated in response to a signal generated when there is a demand for an immediate hydrogen supply to a fuel cell (5). The acid held at a tank (7) is then fed to the reaction vessel (3) through a feed line (8). For example, in response to the issuance of an alarm signal (not shown), a metered amount of the acid is injected into the reaction vessel, driving formate decomposition and hydrogen production at room temperature. The added acid may be supplied to the reaction mixture in the form of an aqueous solution or in a solid form through a solid dosing pump.

As previously explained, using an excessive amount of an acid may lead to the loss of the reversibility of the bicarbonate-formate cycle due to $CO_2$ evolvement. However, the reaction according to equation (2) does not occur, or is at least minimized, when the acid used is formic acid.

In another variant of the process, the decomposition is started at a first temperature $T_1$ below 50° C. in the presence of an acid (e.g., added HCOOH), and on consumption of the acid, the reaction vessel is heated to a second temperature $T_2$ above 50° C., whereby the reaction of formate decomposition reaches completion at a temperature above 50° C.

We have also tested the performance of several palladium on carbon support (Pd/C) catalysts in connection with the bicarbonate-formate cycle and found that high hydrogen storage and production capacity could be achieved with the aid of Pd/C catalyst with Pd loading in the range from 0.15 to 1.0 wt %, preferably 0.2 to 0.5 wt %, characterized in that at least a portion of the palladium is present on the support in the form of sub-nanometer particles (<1 nm). The presence of the sub-nanometer Pd particles in the catalyst sample is indicated by Scanning Transmission Electron Microscopy with Energy Dispersive X-ray Spectroscopy (STEM-EDS), identifying palladium-containing regions in the carbon support, which regions consist of invisible Pd particles (i.e., below TEM resolution and therefore too small to be visible in the TEM image). Additionally, Pd particles in the low nanometer range of size (from 1 nm to 20 nm, e.g., from 1 nm to 5 nm) are also present in the Pd/C catalyst; these particles are visible in TEM images.

Pd/C catalyst with the properties set forth above can be prepared by reduction of palladium salt (e.g., $Pd(NO_3)_2 \cdot 2H_2O$) using a mild reducing agent (for example, potassium formate) over activated carbon. More specifically, the Pd/C catalyst is prepared by a process comprising dissolving in water a palladium salt, such as palladium (II) nitrate dihydrate, adding to the solution heat-treated activated carbon (preferably a form bearing acidic groups, such as C-3345 available from Sigma), stirring the so-formed mixture, reducing the $Pd^{2+}$ to $Pd^0$ under mild conditions (e.g., with the aid of formate, especially potassium formate, as a reducing agent), collecting a powder consisting of Pd/C, washing and drying same.

The reduction step preferably takes place at room temperature. Potassium formate is added to the reaction vessel preferably gradually, e.g. over a period of time of not less than 15 minutes, such that the concentration of potassium formate in the reaction mixture is less than 0.15M, with a concentration from 0.001 to 0.12M, e.g., from 0.005 to 0.01M, being preferred. For example, the molar ratio between the formate and the palladium salt 1:1 to 20:1.

The so-formed Pd/C catalyst, with Pd loading in the range from 0.15 to 1.0 wt %, preferably 0.2 to 0.5 wt %, displays higher activity than commercially available Pd/C 5% catalyst (i.e., with higher Pd loading). The experimental results reported below indicate that hydrogen can be released from potassium formate solution over Pd/C 0.2% of the invention with better TON than when using Pd/C 5%.

The compositional information obtained by the imaging techniques employed for characterizing the Pd/C samples indicates that potassium (from the reductant) is incorporated into the Pd/C catalyst. The potassium appears to be found in the vicinity of Pd particles of the low nanometer range of size. Regions of the Pd/C where the sub-nanometer Pd is present appear to be potassium-free.

The concentrated aqueous formate solution (i.e., with concentration higher than 5M, e.g., from 8M and up to saturation) obtainable from a bicarbonate slurry as described above is a liquid carrier capable of storing hydrogen and releasing same on demand at a site of use. The hydrogen can be put to use within a power system or a vehicle, but also in other applications, such as for filling balloons and airships in the field.

Another aspect of the invention is a power system comprising at least one fuel cell and a hydrogen-generating unit for delivering hydrogen to the anodic compartment of said fuel cell, said hydrogen-generating unit comprising a catalyst-containing composition capable of reversible catalytic hydrogenation and dehydrogenation, which composition is in the form of potassium bicarbonate slurry and a concentrated aqueous potassium formate solution, respectively, wherein said hydrogen-generating unit is provided with a first feed line for introducing an incoming hydrogen stream for hydrogenating said poatassium bicarbonate slurry and a second feed line for introducing an oxidizer (e.g., a stream of pressurized air) into said reaction vessel for regenerating said catalyst, and a discharge line for directing a hydrogen stream generated on dehydrogenating said potassium formate solution to said fuel cell.

FIG. 3 is a schematic illustration of a specific embodiment of the hydrogen-generating unit which could be coupled to a fuel cell (5). A single reaction vessel is used for holding the catalyst-containing composition capable of reversible catalytic hydrogenation and dehydrogenation. The reaction vessel is a pressure reactor (3) equipped with heating and agitation means. The hydrogen-generating unit further comprises a hydrogen source (1) and means for pressurizing hydrogen (2) connected through feed line (9) to the reaction vessel (3). Feed line (10) is used to deliver an oxygen-containing gas, preferably pressurized air, to said pressure reactor (3). As shown in FIG. 3, feed lines (9) and (10) may be joined into a single line. The hydrogen-generating unit may further comprise an acid storage tank (7), for injecting an acid through feed line (8) into the reactor (3). Hydrogen stream released from the composition is guided through line (4) to the fuel cell (5).

EXAMPLES

Example 1

Reversible Hydrogen Absorption Over Potassium Bicarbonate Slurry 23.8 g of Pd/C 5% (51.3% wet, Engelhardt 5.47 mmol) were placed in an autoclave vessel along with 28.9 g of potassium bicarbonate (0.29 mol) and 12.23 g of water. The autoclave was sealed and washed with nitrogen gas 3 times.

Figure 2:
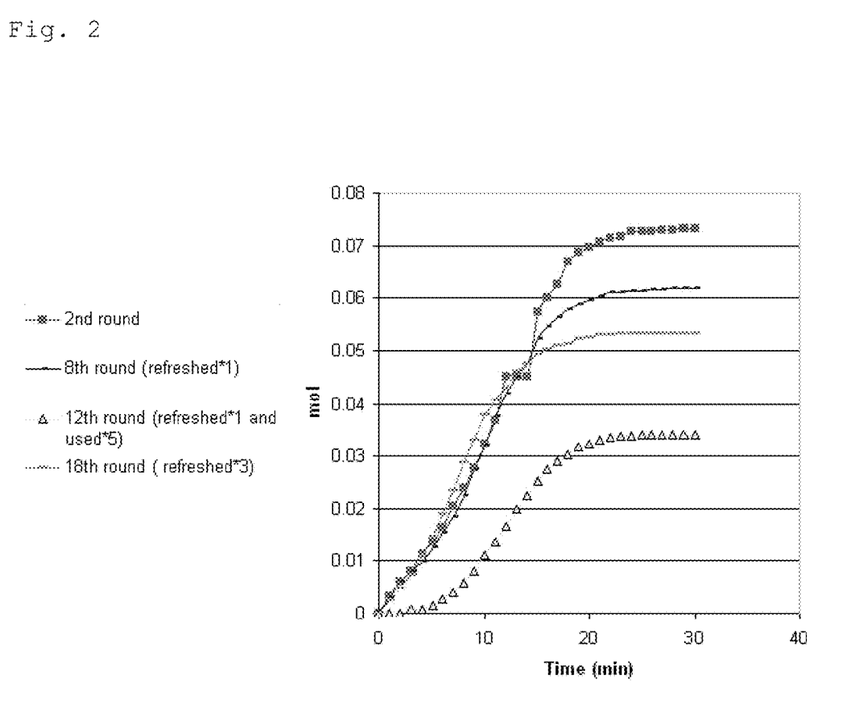
FIG. 2 is a graph showing the effect of catalyst regeneration on the hydrogenation-dehydrogenation cycle.

Hydrogen was added to the autoclave at 35° C. to 9.5 atmospheres and mixed for at least 2 hours. Then the initial pressure was released and gas flow from the autoclave was recorded while heating to 70° C. This cyclic procedure (formate synthesis and formate decomposition) was repeated 7 times without opening the autoclave. Then air was added to the autoclave to 10 atmospheres and heated to 70° C. for 2 hours with stirring in order to refresh the catalyst. After air addition, the autoclave was washed with nitrogen followed by hydrogen. Again hydrogen was loaded and its release was recorded for 5 more rounds, followed by catalyst regeneration under the conditions set forth above. The cyclic procedure was repeated again up to a total of 21 rounds, with the catalyst regeneration step taking place after the seventh, twelfth and seventeenth rounds. The results are graphically presented in FIG. 2, for the $2^{nd}$, $8^{th}$, $12^{th}$ and $18^{th}$ cycles, showing that following the catalyst regeneration according to the treatment of the invention (i.e., the $8^{th}$ and $18^{th}$ cycles), the rate of the reaction is significantly increased.

Example 2

Reversible Hydrogen Absorption Over Potassium Bicarbonate Slurry Using Pd/C 0.4% Catalyst Potassium Bicarbonate Slurry↔10M Potassium Formate Solution A 300 ml autoclave was fed with 4 g of Pd/C 0.4% of Preparation 6 (60% wet, 0.06 mmol), 3 g of potassium bicarbonate (0.03 mol, Sigma 23705) and 1.125 g of deionized water (0.0625 mol). The molar ratio between palladium and bicarbonate is 500:1. The molar ratio between water and bicarbonate is 2.1:1 and it fits the molar ratio between water and formate in a 10M potassium formate solution (the bicarbonate at these conditions is in the state of slurry). The autoclave was purged 3 times with nitrogen gas before hydrogen was allowed to flow into it to a pressure of 9.6 bar. The temperature was set to 35° C. and mechanical stirring (cross impeller) was activated at 400 rpm for 2 hours. After 2 hours the pressure was 8.3 bar. Then the autoclave's faucet was opened to reach rapidly to atmospheric pressure. The autoclave was connected to a water based flow-meter through a Ba(OH)$_2$ trap and heated to 70° C. to release hydrogen.

The foregoing hydrogenation-dehydrogenation procedure was carried out two times, and then the catalyst was reactivated.

Catalyst reactivation: at the end of dehydrogenation the autoclave was purged 3 times with nitrogen at 10 bar and then air was allowed to flow into it to a pressure 10 bar. The autoclave was heated to 70° C. for 2 hours and mechanical stirring (cross impeller) was set to 400 rpm. Then the autoclave's faucet was opened to reach rapidly to atmospheric pressure. The autoclave was purged 3 times with nitrogen at 10 bar before it was charged with hydrogen to a pressure of 9.6 bar and heated to 35° C. for 2 hours. Mechanical stirring (cross impeller) was activated at 400 rpm. Then the autoclave's faucet was opened to reach rapidly to atmospheric pressure. The autoclave was connected to a water based flow-meter through a Ba(OH)$_2$ trap and heated to 70° C. to release hydrogen.

Figure 4A:
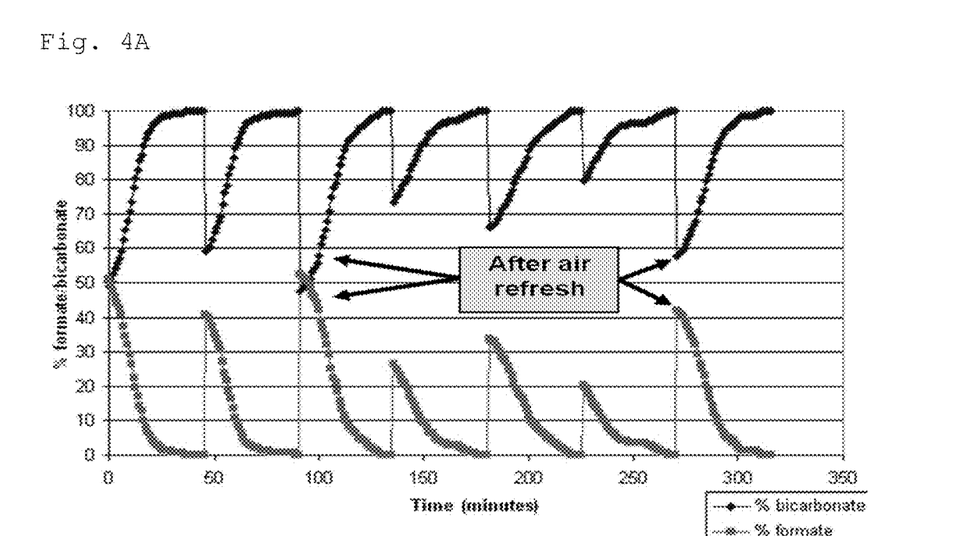
FIGS. 4A and 4B are graphs showing the effect of catalyst regeneration on the hydrogenation-dehydrogenation cycle.

After catalyst reactivation, the cyclic hydrogenation-dehydrogenation procedure was repeated four times, and then the step of catalyst reactivation took place again. Thus, a total of seven cycles were run, with the catalyst regeneration step taking place after the second and sixth rounds. The results are presented in FIG. 4A. The upper line represents bicarbonate concentration and the lower line represents formate concentration.

Potassium Bicarbonate Slurry⇔15.7M Potassium Formate Solution

A 300 ml autoclave was fed with 26.5 g of Pd/C 0.4% of Preparation 6 (60% wet, 0.4 mmol) and 5 g of potassium bicarbonate (0.05 mol, Sigma 23705). The molar ratio between palladium and bicarbonate is 125:1. Hydrogenation of solid bicarbonate to formate without addition of water can theoretically produce 15.7M potassium formate solution (in case all the bicarbonate is hydrogenated to formate and water). The autoclave was purged 3 times with nitrogen gas before hydrogen was allowed to flow into it to a pressure of 9.6 bar. The temperature was set to 35° C. and mechanic stirring (cross impeller) was activated at 400 rpm for 2 hours. After 2 hours the pressure was 8.5 bar. Then the autoclave's faucet was opened to reach rapidly to atmospheric pressure. The autoclave was connected to a water based flow-meter through a Ba(OH)$_2$ trap and heated to 70° C. to release hydrogen.

The foregoing hydrogenation-dehydrogenation procedure was carried out four times, and then the catalyst was reactivated.

Catalyst reactivation: at the end of dehydrogenation the autoclave was purged 3 times with nitrogen at 10 bar and then air was allowed to flow into it to a pressure 10 bar. The autoclave was heated to 70° C. for 2 hours and mechanical stirring (cross impeller) was set to 400 rpm. Then the autoclave's faucet was opened to reach rapidly to atmospheric pressure. The autoclave was purged 3 times with nitrogen at 10 bar before it was charged with hydrogen to a pressure of 9.6 bar and heated to 35° C. for 2 hours. Mechanical stirring (cross impeller) was activated at 400 rpm. Then the autoclave's faucet was opened to reach rapidly to atmospheric pressure. The autoclave was connected to a water based flow-meter through a Ba(OH)$_2$ trap and heated to 70° C. to release hydrogen.

Figure 4B:
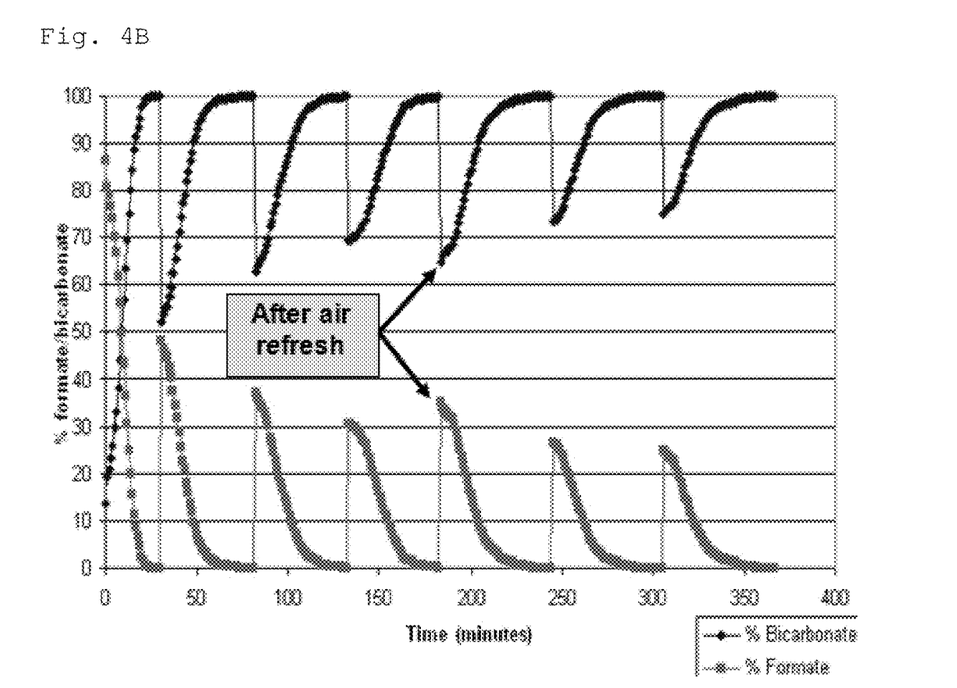

After catalyst reactivation, the cyclic hydrogenation dehydrogenation procedure was repeated three times. Thus, a total of seven cycles were run, with the catalyst regeneration step taking place after the fourth round. The results are presented in FIG. 4B. The upper line represents bicarbonate concentration and the lower line represents formate concentration.

Examples 3 to 9

Formate Decomposition in the Presence of an Acid

To investigate the effect of acidic pH and type of acid on formate decomposition, various acids were added to potassium formate (KHCO$_2$, abbreviated "PF") 4M aqueous solutions in different acid: PF molar ratios and the so-formed acidic solutions went through dehydrogenation over Pd/C at 70° C. (commercial Pd/C 5%, Sigma 205680). The conditions of the reactions and the performance of the catalyst in the acidic environment are tabulated in Table 1.

TABLE 1

| Example | Acid | Ratio (KHCO$_2$:acid:Pd) | pH | TON at deactivation | TOF (min$^{-1}$) |
|---|---|---|---|---|---|
| 3 | HCOOH | 2000:2000:1 | 4 | 264 | 62 |
| 4 | HCOOH | 2000:200:1 | 5 | 1131 | 93 |
| 5 | HCl | 2000:1000:1 | 4 | 172 | 12 |
| 6 | HNO$_3$ | 2000:800:1 | 4 | 330 | 124 |
| 7 | CH$_3$COOH | 2000:5000:1 | 4.5 | 288 | 64 |
| 8 | HNO$_3$ | 2000:200:1 | 6 | 475 | 91 |
| 9 | H$_2$SO$_4$ | 2000:200:1 | 6 | 289 | 78 |

In the absence of an acid, the TON and TOF were ~850 and ~30, respectively. The experimental results set out in Table 1 indicate that the addition of an acid leads to increased TOFs, but in some cases the TONs were lower than can be achieved at neutral media. Formic acid (abbreviated "FA") emerges as especially useful acid for enhancing the decomposition of the formate to give hydrogen. In the experimental work to follow, formic acid was chosen for acidifying the formate solution.

Examples 10 to 16

Formate Decomposition in the Presence Varying Amounts of Formic Acid

The following set of experiments illustrates the effect of the molar ratio between potassium formate and formic acid on formate decomposition. In the tested solutions, the concentration of potassium formate was 4M and the molar ratio potassium formate to palladium catalyst was constant (2000:1). Various amounts of FA were added to these PF 4M aquatic solutions, which went through dehydrogenation over Pd/C 5% (Sigma 205680) at 70° C. The conditions of the reactions and the performance of the catalyst in the presence of formic acid are tabulated in Table 2.

TABLE 2

| Example | Ratio (KHCO$_2$:HCOOH:Pd) | TON at deactivation | TOF (min$^{-1}$) |
|---|---|---|---|
| 10 (comparative) | 2000:0:1 | 846 | 34 |
| 11 | 2000:20:1 | 914 | 47 |
| 12 | 2000:100:1 | 838 | 83 |
| 13 | 2000:200:1 | 1131 | 86 |
| 14 | 2000:350:1 | 716 | 102 |
| 15 | 2000:500:1 | 405 | 102 |
| 16 | 2000:2000:1 | 264 | 62 |

Figure 5:
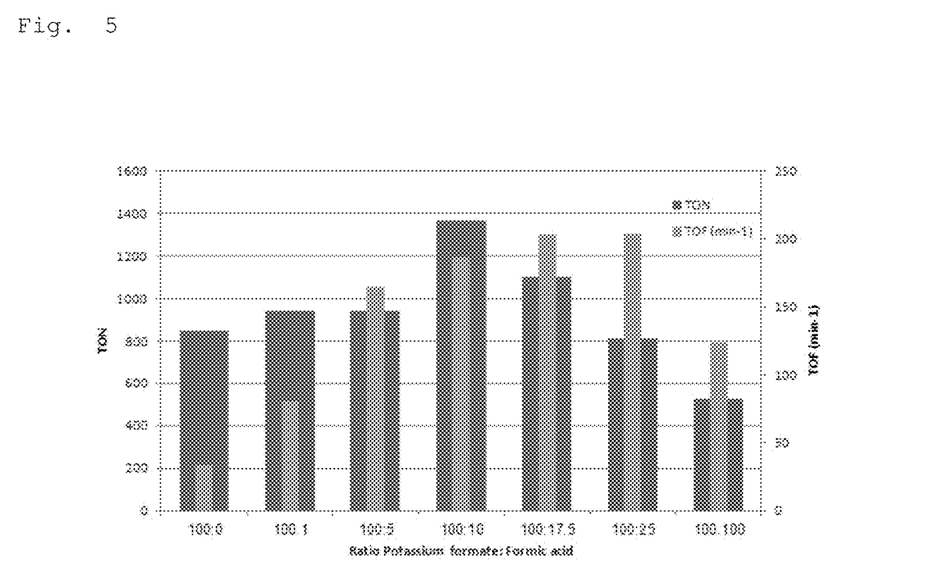
FIG. 5 is a bar diagram showing TON and TOF measured in 4M potassium formate solution with different amounts of formic acid, at 70° C.

The results are also presented in the form of a bar diagram in FIG. 5, where thick and narrow bars indicate the TONs and TOFs, respectively (the left and right ordinate correspond to the TON and TOF, respectively). At an elevated temperature (e.g., T=70°), the decomposition of formate in acidic environment runs most efficiently when the ratio potassium formate to formic acid lies in the range from 10:0.5 to 10:10, especially from 10:1 to 10:5, e.g. from 10:1 to 10:3.

Example 17

Formate Decomposition in a Highly Concentrated Solution in the Presence Formic Acid To illustrate that acidic environment generated by FA is capable of advancing formate decomposition also in highly concentrated PF solutions, FA was added to 16M PF aquatic solution at ratio FA:PF 1:10 (giving a solution of 16M PF, 1.6M FA). This solution went through dehydrogenation over Pd/C (Sigma 205680) at 70° C. Initial TOF=178 min$^{-1}$, TON (at deactivation)=646.

Examples 18-24

Formate Decomposition in Acidic Environment at 25° C.

The ability of formic acid to advance formate decomposition at 25° C. was studied. Various amounts of FA were added to PF 4M aquatic solutions. These solutions went through dehydrogenation over Pd/C (Sigma 205680) at 25° C. The conditions of the reactions and the performance of the catalyst in the presence of formic acid at 25° C. are tabulated in Table 3.

TABLE 3

| Example | PF:FA ratio | TON at deactivation | TOF (min$^{-1}$) |
|---|---|---|---|
| 18 | 10:1 | 259 | 17 |
| 19 | 10:2 | 353 | 32 |
| 20 | 10:3 | 615 | 33 |
| 21 | 10:4 | 752 | 29 |
| 22 | 10:5 | 676 | 31 |
| 23 | 10:6 | 613 | 30 |
| 24 | 10:10 | 313 | 30 |

Figure 6:
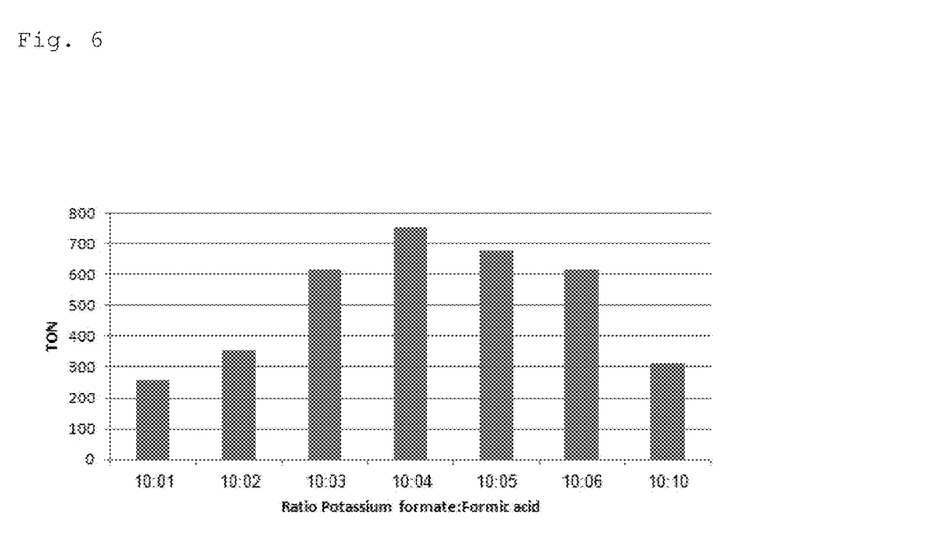
FIG. 6 is a bar diagram showing TON measured in 4M potassium formate solution with different amounts of formic acid, at room temperature.

The results show that the catalytically-driven decomposition of formate progresses satisfactorily even at room temperature, with the aid of formic acid. On graphically presenting the results in a bar diagram, where the abscissa and ordinate are $MR_{PF:FA}$ and TON, respectively, a curve resembling inverted parabola is seen (FIG. 6), with an axis of symmetry in the range of $10:3 < MR_{PF:FA} < 10:5$.

Examples 25-27

Formate Decomposition in Acidic Environment at 25° C.

The experimental procedures set forth in the previous set of examples were repeated, but this time with higher concentration of PA, and correspondingly, with higher concentration of FA. The solutions went through dehydrogenation over Pd/C (Sigma 205680) at 25° C. The conditions of the reactions and the performance of the catalyst in the presence of formic acid at 25° C. are tabulated in Table 4.

TABLE 4

| Example | PF concentration (M) | PF:FA molar ratio | TON at deactivation | TOF (min$^{-1}$) |
|---|---|---|---|---|
| 25 | 12.0 | 10:2 | 519 | 50 |
| 26 | 12.0 | 10:3 | 563 | 88 |
| 27 | 14.5 | 10:1.2 | 344 | 47 |

Figure 7:
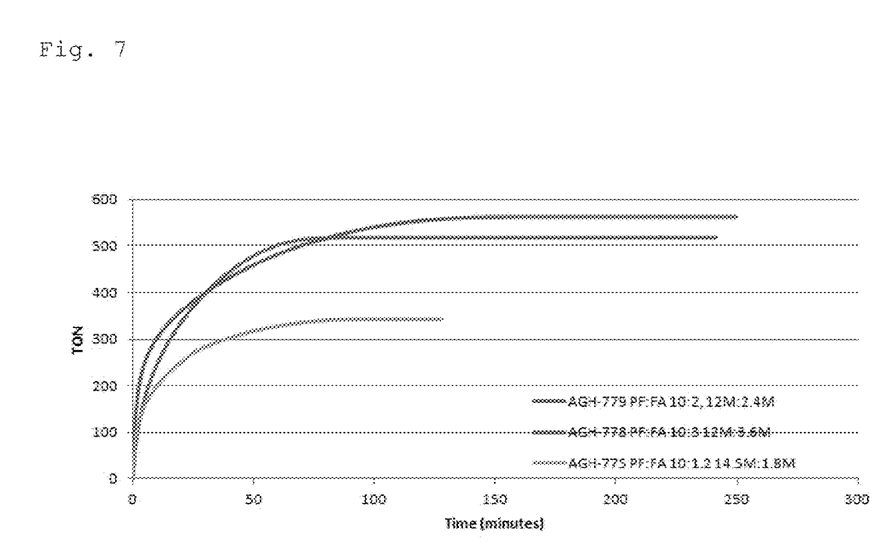
FIG. 7 is a plot of TON against time on dehydrogenating different concentrated potassium formate solutions in the presence of formic acid, at room temperature.

It can be seen that formic acid promotes the catalytically-driven decomposition of highly concentrated formate solutions at room temperature. The results set out in Table 4 are shown graphically in FIG. 7, where the TON is plotted as function of reaction time for each of the three experiments of Examples 25, 26 and 27, illustrating that TONs (at deactivation) higher than 300 are achievable in the very high concentration regimen of formate aqueous systems, with fairly reasonable PF:FA molar ratio.

Example 28

Formate Decomposition in Acidic Environment at 25° C. and in Neutral pH at 70° C.

PF and FA were added to water to form an aqueous solution with PF and PA concentrations of 12.0M and 2.4M, respectively. The catalytically-driven reaction started at room temperature in the presence of Pd/C (Sigma 205680, the catalyst loading was 1:500 relative to the PF). After 90 minutes, the acid was essentially consumed (as indicated by cessation of hydrogen evolution) and the reaction mixture was heated to 70° C. and kept at that temperature for about additional 90 minutes to reach almost full decomposition of the formate.

Figure 8:
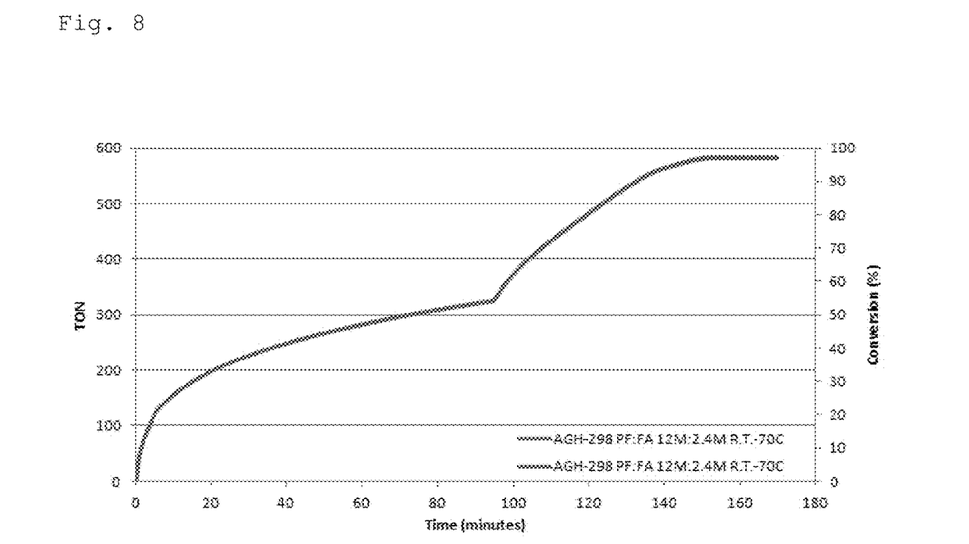
FIG. 8 is a curve showing the TON (left ordinate) and percentage of formate conversion (right ordinate) as function of reaction time, measured at two different temperatures.

A curve showing the TON (left ordinate) and percentage of formate conversion (right ordinate) as function of reaction time is plotted in FIG. 8.

Examples 29-35

Formate Decomposition in Acidic Environment at Different Temperatures

The effect of temperature variation on formate decomposition in an acidic environment induced by formic acid was tested. Aquatic solutions of potassium formate 4M an formic acid 0.8M went through dehydrogenation over Pd/C 5% (Sigma 205680) at a variety of temperatures, as described in Table 5:

TABLE 5

| Example | Temperature (° C.) | TON at deactivation | TOF (min$^{-1}$) |
|---|---|---|---|
| 29 | 0° | 519 | 9 |
| 30 | 10° | 645 | 23 |

TABLE 5-continued

| Example | Temperature (° C.) | TON at deactivation | TOF (min$^{-1}$) |
|---|---|---|---|
| 31 | 20° | 858 | 41 |
| 32 | 30° | 799 | 46 |
| 33 | 40° | 1110 | 85 |
| 34 | 50° | 632 | 63 |
| 35 | 60° | 726 | 101 |

Figure 9:
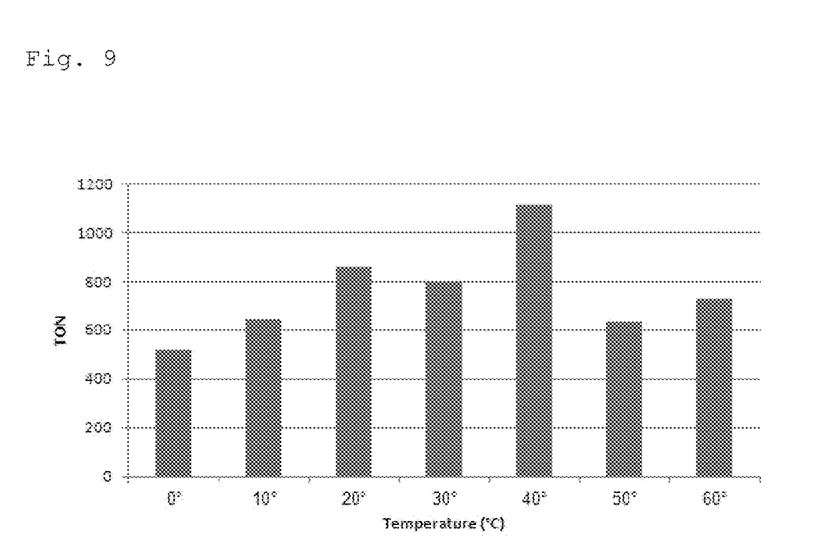
FIG. 9 is a bar diagram showing the dehydrogenation of potassium formate solution in the presence of formic acid at different temperatures.

A bar diagram showing the results of TON at deactivation as function of temperature is given in FIG. 9.

Examples 36-37

Hydrogen Release from Potassium Formate Solution over Pd/C 0.2% and Commercial Pd/C 5%

Figure 10:
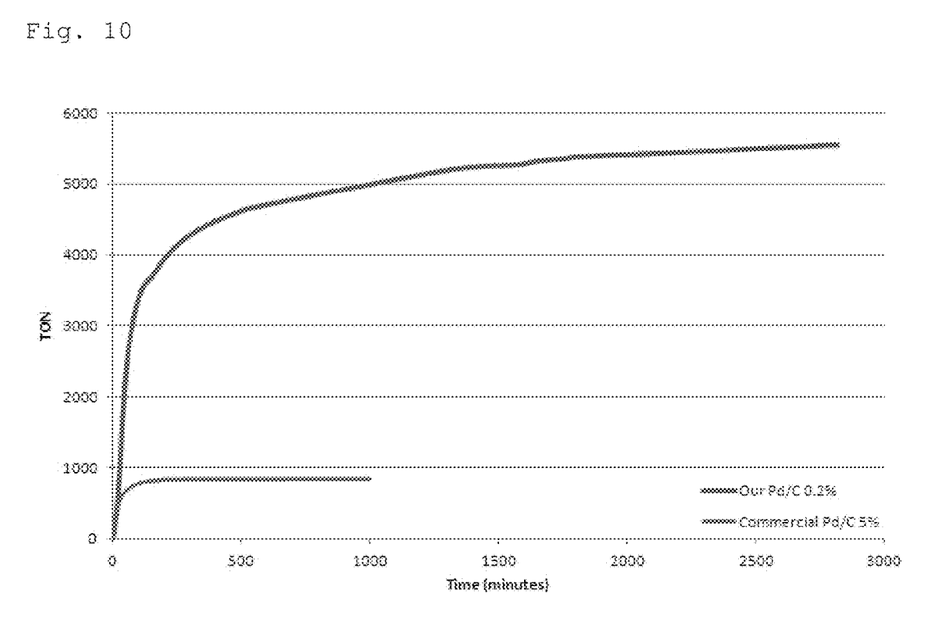
FIG. 10 is a graph showing TON measured on dehydrogenating potassium formate solution with different Pd/C catalysts.

10 ml of 4M solution was prepared by addition of water to 3.3648 g (0.04 mol) of potassium formate. The solution was added to 0.59 g of Pd/C 0.2% (40% wet, 0.0067 mmol) of Preparation 7 or 0.014 g of Pd/C 5% (Sigma 205680, 0.0067 mmol) and went through dehydrogenation at 70° C. (formate: Pd molar ratio of 6000: 1). The profile of the reaction is illustrated in the graph of FIG. 10, where the turn over number (TON) is plotted against time. The results indicate that hydrogen can be released from potassium formate solution over Pd/C 0.2% with TON over 7 times better than when using Pd/C 5%.

Preparation 1

Supported Palladium Catalyst

CNT (commercial multiwall carbon nano-tubes) or activated carbon was placed in a flask with isopropyl alcohol (IPA). The mixture was subjected to sonication for a total of 20 minutes (activation periods of one seconds each, with an intermission of one second between each activation period). Palladium acetate solution in IPA was prepared and added to the flask. The flask was heated to reflux (85° C.) for 3 hours followed by evaporation of the IPA. The content of the flask was dried for 1 hour under vacuum at 65° C.

Preparation 2

Supported Palladium Catalyst

Montmorillonit k-10 and di-n-decyldimethylammonium bromide were placed in a flask (weight ratio ammonium salt:mineral 5:3). Ethanol was added as a solvent for the ammonium salt.
The mixture was stirred at room temperature for 3 hours and then filtered and washed with ethanol. The ammonium salt absorbed-montmorillonit was placed in water with palladium (II) nitrate (weight ratio palladium: mineral 1: 9). The mixture was stirred for 18 hours, then filtered, washed with water and dried at vacuum at 60° C.

Preparation 3

Supported Palladium Catalyst

Palladium (II) acetate was dissolved in acetone. CNT or activated carbon was added to the solution according to the desired percentage of palladium. The mixture was stirred while aquatic solution of hydrazine was added dropwise for 30 minutes. The mixtures were left over night and filtered by gravitation the next morning.

Preparation 4

Supported Palladium Catalyst

CNT, activated carbon or PANI (polyaniline) was placed in water with palladium (II) nitrate. A reductive agent such as hydrazine solution or sodium borohydride aquatic solution was added dropwise for 30 minutes. The mixture was stirred for 18 hours, then filtered, washed with water and dried at vacuum at 60° C.

Preparation 5

Supported Palladium Catalyst

CNT, activated carbon or PANI (polyaniline) was placed in water with palladium (II) nitrate. Hydrogen gas was added to 9.5 atmospheres for 2 hours at room temperature. Then the mixture was filtered, washed with water and dried at vacuum at 60° C.

Preparation 6

Supported Palladium Catalyst

Palladium (II) nitrate dihydrate (0.096 mmol, Sigma 76070) was dissolved in water (1 L). Activated carbon (Sigma C-3345) was heated to 200° C. for 1 hour. The treated activated carbon (25 g in order to get 0.4% Pd/C) was added into the palladium solution and stirring was activated to 700 rpm for 1 hour. Then an aqueous solution of potassium formate (0.081 g in 200 ml of water) that was used as a reduction agent was added dropwise for 30 minutes at 25° C. (molar ratio between palladium and reduction agent is 10:1, total concentration of formate in the vessel was 0.008M). Following that the mixture was left while stirring continued at room temperature for 24 hours. After 24 hours the mixture was filtered, washed thoroughly with deionized water and left to dry at room temperature.

Preparation 7

Supported Palladium Catalyst

Figure 11:
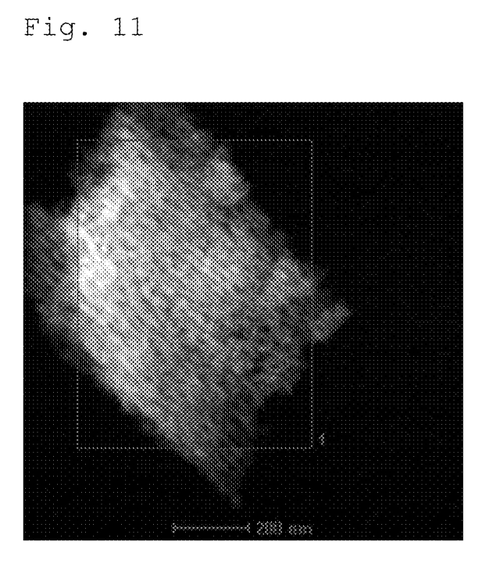
FIG. 11 is a STEM picture of Pd/C 0.2% prepared by formate reduction.
Figure 12:
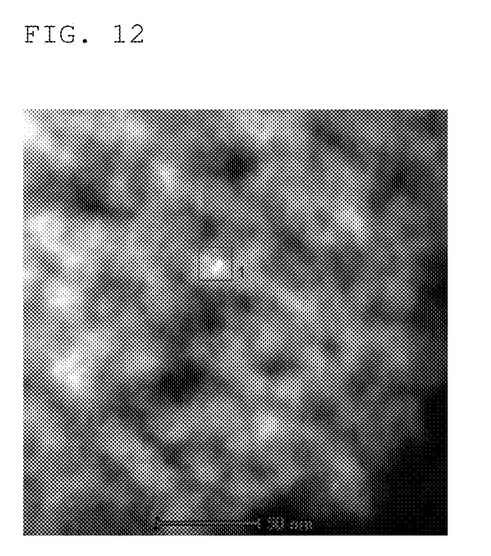
FIG. 12 is a STEM picture of Pd/C 0.2% prepared by formate reduction.

Pd/C 0.2% was prepared using a procedure similar to that of Preparation 6, i.e., via formate reduction of Pd$^{2+}$ under mild conditions, but this time 0.5 g of the treated activated carbon were added to the palladium salt solution to achieve the 0.2% loading.
The Pd/C powder collected was subjected to STEM-EDS analysis [Tecnai F20 G2 (FEI company)]. FIG. 11 is a STEM image showing a region of the Pd/C sample which contains palladium (36.3%). The Pd particles in the region observed are invisible, indicating that the palladium present in that region consists of sub-nanometer Pd particles (below TEM resolution). There was no indication of the presence of potassium in the sub-nanometer Pd particles regions.
On the other hand, in the STEM image of FIG. 12, another region of the Pd/C sample is shown, where Pd particles in the low nanometer range of size (from 1 nm to 5 nm) are identified. Compositionally, the palladium content is 65.59% and the potassium content is 0.55% (w/w).

The invention claimed is:

1. A process for the production of hydrogen, comprising catalytically decomposing a concentrated aqueous solution of potassium formate in a reaction vessel to form bicarbonate slurry and hydrogen, discharging the hydrogen from said reaction vessel, and treating a mixture comprising the bicarbonate slurry and the catalyst with an oxidizer, thereby regenerating the catalyst.

2. A process according to claim 1, wherein the decomposition of the formate takes place at a temperature above 50° C.

3. A process according to claim 1, wherein the decomposition of the formate takes place at a temperature below 50° C., in the presence of an acid.

4. A process according to claim 3, wherein the acid is formic acid.

5. A process according to claim 3, wherein the decomposition of the formate takes place at ambient temperature.

6. A process according to claim 5, wherein the molar ratio between potassium formate and formic acid is in the range from 10:1 to 10:10.

7. A process according to claim 1, wherein the decomposition of the formate is started at a first temperature $T_1$ below 50° C. in the presence of an acid, and on consumption of the acid, the reaction vessel is heated to a second temperature $T_2$ above 50° C.

8. A process according to claim 7, wherein $T_1$ is ambient temperature.

9. A process according to claim 1, wherein the concentration of the potassium formate solution is not less than 8M.

10. A process according to claim 1, wherein the potassium bicrbonate slurry is treated with air or oxygen, to regenerate the catalyst.

11. A process according to claim 1, wherein the concentrated aqueous solution of potassium formate is prepared by catalytically hydrogenating a potassium bicarbonate slurry.

12. A process for storage and subsequent release of hydrogen, comprising:
  (i) catalytically hydrogenating in a reaction vessel potassium bicarbonate slurry to form a concentrated aqueous solution of potassium formate;
  (ii) catalytically decomposing said formate solution in a reaction vessel to form bicarbonate slurry and hydrogen;
  (iii) discharging the hydrogen from said reaction vessel; and
  (iv) treating a mixture comprising the bicarbonate slurry and the catalyst with an oxidizer, thereby regenerating said catalyst.

13. A process according to claim 1, wherein the catalyst is palladium on carbon support (Pd/C), with palladium loading from 0.15 to 1.0%, characterized in that at least a portion of the palladium is in the form of sub-nanometer particles.

14. A process according to claim 13, wherein the Pd/C catalyst is prepared by the reduction of a palladium salt, with potassium formate as reductant, over activated carbon.

15. A process for the storage of hydrogen, comprising treating a mixture of potassium bicarbonate slurry and a catalyst with an oxidizer, and catalytically reducing said bicarbonate slurry in a reaction vessel to form a concentrated aqueous solution of potassium formate.

16. A process comprising subjecting a potassium bicarbonate slurry, in admixture with catalyst particles, to heterogeneous catalytic hydrogenation of potassium bicarbonate to form potassium formate.

17. A power system comprising at least one fuel cell and a hydrogen-generating unit for delivering hydrogen to the anodic compartment of said fuel cell, said hydrogen-generating unit comprising a catalyst-containing composition capable of reversible catalytic hydrogenation and dehydrogenation, which composition is in the form of potassium bicarbonate slurry and a concentrated aqueous potassium formate solution, respectively, wherein said hydrogen-generating unit is provided with a first feed line for introducing an incoming hydrogen stream for hydrogenating said poatassium carbonate slurry and a second feed line for introducing an oxidizer into said reaction vessel for regenerating said catalyst, and a discharge line for directing a hydrogen stream generated on dehydrogenating said potassium formate solution to said fuel cell.

* * * * *